United States Patent [19]

Muller

[11] Patent Number: 4,856,513

[45] Date of Patent: Aug. 15, 1989

[54] LASER REPROFILING SYSTEMS AND METHODS

[75] Inventor: David F. Muller, Boston, Mass.

[73] Assignee: Summit Technology, Inc., Watertown, Mass.

[21] Appl. No.: 19,200

[22] Filed: Mar. 9, 1987

[51] Int. Cl.$^4$ .............................................. A61F 9/00
[52] U.S. Cl. ................................ 128/303.1; 350/363; 219/121.60
[58] Field of Search .......................... 128/303.1, 395; 350/363; 340/795, 796; 219/121 C, 121 CH, 121 LJ, 121 LM, 121.60

[56] References Cited

U.S. PATENT DOCUMENTS

| | | |
|---|---|---|
| 3,262,122 | 5/1963 | Fleisher et al. |
| 3,558,208 | 1/1971 | Hudson ............................ 350/314 |
| 3,588,439 | 6/1971 | Heller et al. ...................... 219/121 |
| 3,665,483 | 5/1972 | Becker et al. ..................... 219/121 |
| 3,703,176 | 11/1972 | Vassilliadis et al. .............. 128/394 |
| 3,739,088 | 6/1973 | Landsman ......................... 219/121 |
| 3,769,963 | 11/1973 | Goldman et al. ................. 128/2 R |
| 3,889,272 | 6/1975 | Low et al. ......................... 214/121 |
| 3,941,973 | 3/1976 | Luck, Jr. et al. .................. 219/121 |
| 4,046,986 | 9/1977 | Barker ........................... 214/121 LM |
| 4,139,409 | 2/1979 | Macken et al. ............. 214/221 LM |
| 4,173,980 | 11/1979 | Curtin ............................. 128/303 R |
| 4,266,549 | 5/1981 | Kimura ........................... 128/303.1 |
| 4,309,998 | 1/1982 | Aaron nee Rosa et al. ...... 128/303.1 |
| 4,326,529 | 4/1982 | Doss et al. ....................... 128/303.1 |
| 4,381,007 | 4/1983 | Doss ................................ 128/303.1 |
| 4,388,517 | 6/1983 | Schulte et al. ................ 214/121 LJ |
| 4,414,059 | 11/1983 | Blum et al. ................... 219/121 LM |
| 4,461,294 | 7/1984 | Baron .............................. 128/303.1 |
| 4,527,043 | 7/1985 | Hashiura et al. ................... 219/121 |
| 4,538,608 | 9/1985 | L'Esperance, Jr. ............... 128/303.1 |
| 4,648,400 | 3/1987 | Schneider et al. ............... 128/303.1 |
| 4,665,913 | 5/1987 | L'Esperance, Jr. ............... 128/303.1 |
| 4,669,466 | 6/1987 | L'Esperance .................... 128/303.1 |
| 4,686,979 | 8/1987 | Gruen et al. ..................... 128/303.1 |
| 4,732,148 | 3/1988 | L'Esperance, Jr. ............... 128/303.1 |

FOREIGN PATENT DOCUMENTS 111060 9/1983 European Pat. Off.
152686 12/1984 European Pat. Off.
3148748 12/1981 Fed. Rep. of Germany.
3535072 9/1987 Fed. Rep. of Germany.
3535073 9/1987 Fed. Rep. of Germany.
WO86/0450-00 8/1986 World Int. Prop. O.

OTHER PUBLICATIONS

"Coating protection for laser cutting and welding operations" by Rosenbaum et al; IBM Tech. Discl Bull; vol. 18, No. 176 p. 2531.

"Microfilm by Laser Imaging Employing Sublimable Dyes" by Crooks et al,·IBM Tech Discl. Bull.; vol. 19, No. 1 6/76 p. 285.

"Chip Pasaivation Technique" by Coullahan et al., IBM Tech Discl. Bull. vol. 22, No. 6 11/79 pp. 279-281.

Fine et al., "Preliminary Observations On Ocular Effects ...", vol. 64, No. 2, *American Journal of Ophthalmology*, pp. 209-222 (Aug. 1967).

Beckman, et al., "Limbectomies, Keratectomies, And Keratostomies Performed ..." vol. 71, *American Journal of Ophthalmology*, pp. 1277-1283 (Jun. 1971).

(List continued on next page.)

Primary Examiner—Lee S. Cohen
Assistant Examiner—David Shay
Attorney, Agent, or Firm—Thomas J. Engellenner

[57] ABSTRACT

A laser system for reprofiling a surface (18) comprising a laser (10) and an erodible mask (14) disposed between the laser and the surface (18) for providing a predefined profile of resistance to erosion by laser radiation, and a controller (22) for controlling the laser such that upon irradiation of the mask (14), a portion of the laser radiation is selectively absorbed and another portion is transmitted to the surface in accordance with the mask profile to selectively erode the surface. The mask can further comprise a rigid structure (30) which is affixed to the surface, in particular to the sclera of an eye, and a masking lens (36) connected to the support structure and disposed above the cornea. The masking lens can be directed integrated with the support structure or, preferably, a transparent stage (34) can be formed as part of the support structure to support and position the masking lens.

5 Claims, 2 Drawing Sheets

OTHER PUBLICATIONS

Mainster, "Ophthalmic applications of infrared lasers—thermal considerations" vol. 18, No. 4, Invst. Ophthal. and Vis. Sci., pp. 414–420 (1979).

Peyman, et al, "Modification of Rabbit Corneal Curvature With Use of Carbon Dioxide Laser Burns", vol. 11, No. 5, *Ophthalmic Surgery*, pp. 325–329 (May 1980).

Keates et al., "Carbon Dioxide Laser Beam Control for Corneal Surgery", vol. 12, No. 2, *Ophthalmic Surgery*, pp. 117–122, (Feb. 1981).

Girard, "Refractive Keratoplasty", vol. 2, *Corneal Surgery*, pp. 142–171 (1981).

Taboada et al., "Response Of The Corneal Epithelium TO KrF Excimer Laser Pulses", vol. 40, *Health Physics*, pp. 677–683 (May 1981).

Chetverukhin et al., "Refraction Thermokeratoplasty and Laser Keratoplasty", *Vestn. Oftal.*, pp. 67–69 (USSR 1982).

Srinivasan et al., "Far-UV Photoetching of Organic Material", *Laser Focus*, (May 1983).

Srinivasan, "Kinetics of the ablative photodecomposition of organic polymers . . . ", vol. B1, *J. of Vac. Sci. Technol.*, pp. 923–926 (1983).

Srinivasan, "Action of Far-Ultraviolet Light on Organic Polymer Films . . . ", pp. 12–14 (Oct. 1983).

Trokel, et al. "Excimer Laser Surgery of the Cornea", vol. 96, *American Journal of Ophthalmology*, pp. 70–715 (1983).

Galbavy, "Use of Diamond Knives in Ocular Surgery", vol. 15, No. 3, *Opthalmic Surgery*, pp. 203–205 (Mar. 1984).

Puliafito et al., "Excimer Laser Ablation of the Cornea and Lens", vol. 92, No. 6, *Ophthalmology*, pp. 741–748 (Jun. 1985).

L'Esperance, Jr., "New laser systems and their potential clinical usefulness", *Trans. New Orleans Acad. of Ophthalmol.*, pp. 182–209 (1985).

L'Esperance, Jr., "Current status of ophthalmic photovaporization therapy", *Trans. New Orleans Acad. of Ophthalmol,* pp. 231–255 (1985).

O'Hara et al., vol. 11 *IBM Technical Disclosure Bulletin*, pp. 1168–1169 (1969).

LASER REPROFILING SYSTEMS AND METHODS

BACKGROUND OF THE INVENTION

This invention relates to an apparatus and method employing a laser, especially a pulsed laser, for shaping surfaces, especially surfaces of organic material. In particular, the invention relates to an apparatus and method for shaping biological tissue, including the cornea of the eye.

It is known to employ laser sources to erode surfaces of workpieces and the like. Such apparatus is in general relatively complex and demands highly skilled use. It is an object of the present invention to provide improved and simplified apparatus and method for eroding surfaces.

It is also an object of the present invention to provide an improvement whereby laser techniques can be applied to sensitive surfaces and, in particular, to objects in which it would be undesirable to affect underlying layers.

In the field of medicine, a known technique for the treatment of certain forms of myopia is surgically to remove a segment of the collagen sub-surface layer of the eye, to reshape the removed segment as by surgical grinding, and to restore the reshaped segment in the eye. The eye heals by reformation of the outer cellular layer over the reshaped collagen layer. Alternatively, a layer of the cornea is opened up as a flap, an artificial or donor lenticular implant is inserted under the flap, and the flap is sutured up again.

It is a further object of this invention to provide an improved and less traumatic method and apparatus for reshaping the cornea of the eye.

Various other surgical techniques for reprofiling of the corneal surface have also been proposed. One increasingly common technique is radial keratotomy, in which a set of radial incisions, i.e., resembling the spokes of a wheel, are made in the eye to remedy refractive errors such as myopia (nearsightedness). As the incisions heal, the curvature of the eye is flattened, thereby increasing the ocular focal distance. The operation is not particularly suitable for correction of hyperopia (farsightedness) and can pose problems if the surgical incisions are uneven or too deep.

The use of a laser beam as a surgical tool for cutting incisions, a so-called "laser scalpel", has been known for some time (see, for example, U.S. Pat. No. 3,769,963 to Goldman et al.). In 1980, a study was made of the damage which might be inflicted on the corneal epithelium by exposure to the recently developed excimer laser (see Taboada et al., "Response of the Corneal Epithelium to DrF excimer laser pulses" *Health Physics* 1981, Volume 40, pp. 677–683). At that period, surgical operations on the cornea were commonly carried out using diamond or steel knives or razor, and further, such techniques were still being studied (see, for example, Binder et al., "Refractive Keratoplasty" *Arch. Ophthalmol.* May 1982, Vol. 100, p. 802). The use of a physical cutting tool in corneal operations, and the insertion of an implant under a flap, continue to be widely practiced up to the present day (see for example "Refractive Keratoplasty improves with Polysulfone, Pocket Incision" *Ophthalmology Times.* July 1, 1986).

It has been suggested in European Patent Application No. 0151869 of L'Esperance that controlled ablative photodecomposition of one or more selected regions of a cornea can be performed using a scanning action on the cornea with a beam from an excimer laser. Because of the scanning action, it is necessary for L'Esperance to bring his laser beam to a small spot, typically a rounded-square dot of size 0.5 mm by 0.5 mm.

L'Esperance suggests that myopic and hyperopic conditions can be reduced by altering the curvature of the outer surface of the cornea by repeatedly scanning the cornea with an excimer laser beam having this standard, small spot size but varying the field which is scanned during successive scans, so that some areas of the cornea are scanned more often than others. In this way, it is claimed that the surface can be eroded by different amounts depending on the number of times they are scanned by the spot. Additionally, he suggests that certain severe myopic and hyperopic conditions may be treated with a reduced removal of tissue by providing the outer surface of the cornea with a new shape having Fresnel-type steps between areas of the desired curvature.

In practice, complex apparatus is required to cause a laser beam to scan with the precision required if the eroded surface is to be smooth. Thus, if successive sweeps of a scan overlap, there will be excessive erosion in the overlap area, whereas if they fail to meet, a ridge will be left between the sweeps. The compression of the excimer laser beam to a small spot will increase the beam energy density, which will tend to exacerbate these problems. It is not clear that L'Esperance has found a suitable scanning system, since in one embodiment he attempts to control the laser beam by a magnetic field.

Additionally, the scanning method is inherently time-consuming even with highly refined techniques and apparatus, since the laser beam is only eroding a very small part of the total area to be treated at any given moment. Furthermore, such a scanning system can cause rippling effects on relatively soft materials such as corneal tissue.

It is therefore a further object of the present invention to provide a method and apparatus for eroding a surface using a laser which does not require scanning of the area of the surface to be eroded.

Another technique for corneal reshaping involves the use of a laser photoablation apparatus in which the size of the area on the surface, to which the pulses of laser energy are applied, is varied to control the reprofiling operation. In one preferred embodiment, a beam-shaping stop or window is moved axially along the beam to increase or decrease the region of cornea on which the laser radiation is incident. By progressively varying the size of the exposed region, a desired photoablation profile is established in the surface. For further details on this technique see also, Marshall et al., "Photo-ablative Reprofiling of the Cornea Using an Excimer Laser: Photorefractive Keratoctomy", Vol. 1, *Lasers in Ophthalmology*, pp. 21–48 (1986) herein incorporated by reference.

Although this technique for varying the size of the exposed region is a substantial improvement over physical shaping (i.e., scalpel) techniques and laser spot scanning protocols, a considerable number of optical elements and control systems still are required for precise operation, particularly on human corneal tissue. There exists a need for better and simpler procedures for shaping surfaces, particularly the surfaces of biological tissues, such as corneal tissue.

SUMMARY OF THE INVENTION

According to one aspect of the present invention, there is provided a laser system for reprofiling a surface comprising a laser means and a masking means disposed between the laser means and the surface for providing a predefined profile of resistance to erosion by laser radiation, and control means for controlling the laser such that upon irradiation of the masking means, a portion of the laser radiation is selectively absorbed and another portion is transmitted to the surface in accordance with the mask profile to selectively erode the surface.

The masking means can further comprise a rigid structure which is affixed to the surface, in particular to the sclera of an eye, and a masking lens connected to the support structure and disposed above the cornea. The masking lens can be directly intergrated with the support structure or, preferably, a transparent stage can be formed as part of the support structure to support and position the masking lens.

The masking lenses of the present invention provide a predefined profile of resistance to erosion by laser radiation. Such profiles can be provided by varying the thickness or composition of the lens material. When the thickness of the lens is varied, and dependent on the nature of the erosion of the object which is required and the form of the transparent stage, the lens may be convexo-concave, plano-convex, plano-concave, convexo-convex or concavo-concave, and it may also be aspheric or torroidal at least on one surface. In special cases such as the removal of ulcers the surface shape may be irregular.

Conveniently, the lens material has similar ablation characteristics to the object material. Various polymeric materials can be employed including, for example, poly(methyl methacrylate), poly(methyl styrene) and mixtures thereof. For corneal reprofiling, the ablation characteristics of the masking material can range from about $10^3$ to about $10^6 cm^{-1}$. Preferably, the masking material has an absorption characteristic of micron or submicron etch depths per pulse similar to those of the cornea when it is exposed pulsed UV excimer laser radiation.

According to another aspect of the invention, there is provide a method of reprofiling a surface comprising (a) locating a laser means relative to an optical axis of a surface, the laser means being operable to deliver laser radiation to the surface; and (b) disposing a masking means between the laser means and the surface, the masking means having a predefined profile of resistance to erosion by laser radiation such that upon irradiation a portion of the radiation is selectively absorbed and another portion is transmitted to the surface in accordance with the mask profile to selectively erode the surface.

The methods of the present invention are particularly well suited for controlled reprofiling of the cornea, particularly the collagen sub-layer thereof which lies immediately below the uniform, extremely thin, epithelial layer of the cornea, which is very rapidly ablated on exposure to the laser light. The extremely thin surface layer heals and eventually reforms following the reshaping operation. In surgical applications, the laser light is of a wavelength obtainable from a UV Argon Fluoride laser, typically about 193 nanometers, which does not penetrate through the cornea. A minimum laser irradiance level is essential for ablation, but it is preferred not greatly to exceed this minimum threshold.

The pulse repetition rate for the laser may be chosen to meet the needs of each particular application. Normally, the rate will be between 1 and 500 pulses per second, preferably between 1 and 100 pulses per second.

Suitable irradiation intensities vary depending on the wavelength of the laser, and the nature of the irradiated object. For any given wavelength of laser energy applied to any given material, there will typically be a threshold value of the energy density below which significant erosion does not occur. Above the threshold density, there will be a range of energy density over which increasing energy densities give increasing depths of erosion, until a saturation value is reached. For increases in energy density above the saturation value, no significant increase in erosion occurs.

The threshold value and the saturation value will vary from wavelength to wavelength of laser energy and from material to material of the surface to be eroded. However, for any particular laser and any particular material, the values can be found readily by experiment. For example, in the case of eroding a mask and the underlying corneal stroma (collagen sub-layer) by energy of wavelength 193 nm (the wavelength obtained from an ArF excimer laser), the threshold value is about 50 mJ per $cm^2$ per pulse, and the saturation value is about 250 mJ per $cm^2$ per pulse. There appears to be little benefit in exceeding the saturation value by more than a small factor, and suitable energy densities at the corneal surface are 50 mJ per $cm^2$ to one J per $cm^2$ per pulse for a wavelength of 193 nm.

The threshold value can vary very rapidly with wavelength, and at 157 nm, which is the wavelength obtained from a $F_2$ laser, the threshold is about 5 mJ per $cm^2$ per pulse. At this wavelength, suitable energy densities at the corneal surface are 5 mJ per $cm^2$ to one J per $cm^2$ per pulse.

Most preferably, the laser system is used to provide an energy density at the surface to be eroded of slightly less than the saturation value. Thus, when eroding the cornea with a wavelength of 193 nm (under which conditions the saturation value is 250 mJ per $cm^2$ per pulse), it is preferable to provide to the erodible mask and cornea pulses of an energy density single pulse will erode a depth in the range 0.1 to 1 micrometer of collagen from the cornea.

The invention will next be described in connection with certain illustrated embodiments; however, it should be clear that those skilled in the art can make various modifications, additions and subtractions without departing from the spirit or scope of the invention. For example, the invention can be used in connection with corneal transplants where a donor insert is stitched into the patient's eye. Quite often, accidental over-tightening of the stitches introduces refractive errors in the cornea following the operation. At present, the transplant operation must be repeated or relaxing incisions must be made in the cornea. The present invention can provide an improved and less traumatic method for remedying such refractive errors.

Additionally, the present invention can be applied to the remedy of stigmatisms, corneal ulcers and keratomic growths which affect vision. In such instance, specific masks can be designed and constructed to selectively remove the corneal tissue which interfere with normal refraction.

Moreover, the teaching of the present invention can be applied to other biological tissues requiring reprofiling including, for example, ligaments, cartilage, and bone.

BRIEF DESCRIPTION OF THE DRAWINGS

The invention will now be described by way of example with reference to the accompanying drawings, in which.

DETAILED DESCRIPTION

Figure 1:
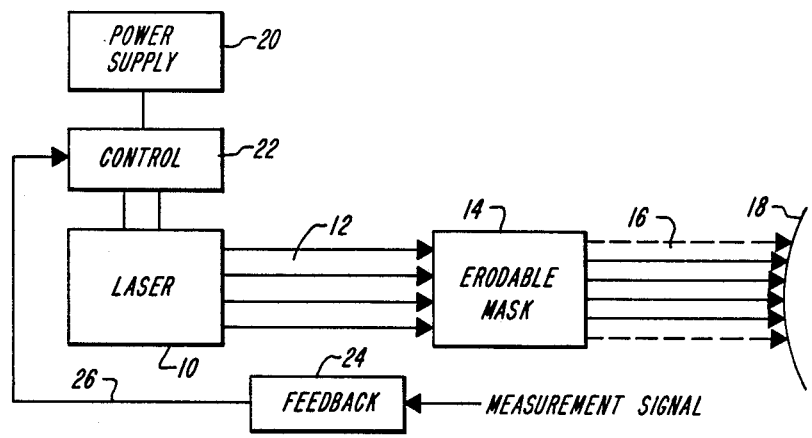
FIG. 1 is a diagramatic illustration of an apparatus for practicing a method of reprofiling the surface of an object, in accordance with the invention.

In FIG. 1, a laser 10 provides a radiation output 12 to an erodible mask 14 which provides a predefined profile of resistance to the radiation. A portion of the laser radiation 16 is selectively transmitted in accordance with the profile of mask 14 and irradiates the surface 18 of the object which is to be reprofiled and which as shown may comprise the cornea of an eye.

The laser is powered by a power supply unit 20 and control circuit 22 which can be adjustable to cause the laser to produce pulses of light at a specific frequency and intensity. To further control the laser, a feedback device 24 can be provided which receives information from optical or other inspection of the mask 14 and/or surface 18 while it is exposed to irradiation by the laser 10. A feedback path 26 communicates with the control circuit 22 for controlling the laser 10.

Figure 2:
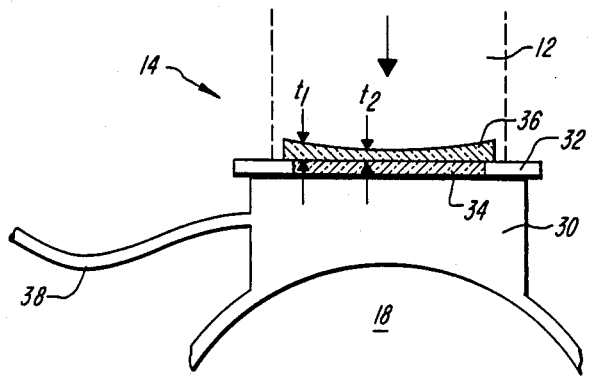
FIG. 2 is a more detailed illustration of an erodible mask suitable for use in the apparatus of FIG. 1.

In FIG. 2, one embodiment of the erodible mask 14 of FIG. 1 is shown in more detail. As illustrated, the erodible mask 14 includes a suction cup 30 which provides a support structure having rigid vertical walls and a horizontal surface 32. At least a portion of the horizontal surface 32 is formed by a transparent stage 34. Preferably, the remainder of surface 32 is opaque to laser radiation. Disposed upon the transparent stage 34 is masking lens 36.

The entire structure can be placed upon the surface of the object, i.e., the sclera of an eye, leaving the corneal surface 18 unobstructed. A flexible tube 38 supplies vacuum suction to the cup, so as to clamp it to the eye with a force sufficient to hold it in place but not distort the shape of the cornea.

The erodible mask 14 can be rigidly connected to the laser or otherwise optically aligned therewith such that radiation from the laser can be selectively transmitted through the mask to produce the desired erosion of the surface by pulses of laser energy.

The selected lens material is a material which is erodible by laser radiation and preferably has ablation characteristics substantially identical to the object material. For example, the erodible masks of the present invention can be formed from plastic material such as poly(-methyl pethacrylate) (PMMA) or poly(methyl styrene) (PS). These polymers are both bio-compatible and can be efficiently eroded by laser radiation, i.e., by a pulsed ArF excimer laser (193 nm). These polymers are mutually soluble in each other, and by changing the concentration of PS in PMMA, absorption coefficients can be varied from about $10^3$ to about $10^6$ cm$^{-1}$. Other organic polymers exhibiting suitable ablation characteristics can also be be employed in the manufacture of erodible masks. Preferably, the polymeric material has an absorption characteristic of micron or submicron etch depths per pulse similar to those of the cornea. For further details on organic polymers suitable for construction of masks, see Cole et al., "Dependence of Photo-etching Rates of Polymers at 193 nm on Optical Absorption Coefficients", Vol. 48 *Applied Physics letters,* pp. 76-77 (1986), herein incorporated by reference.

Various techniques can be employed to manufacture the lenses used in the present invention from PMMA or PS. These techniques included injection molding, casting, machining and spin casting. Manufacture by laser machining can also be employed. In one typical technique, a solution of PMMA or PS is prepared in toluene and spin cast in a suitably-shaped cup to obtain a smooth, uniform lens having a pre-defined profile thickness. Depending upon the concentration of PS in PMMA, a suitable absorption coefficient is obtained. The films can then be removed from the spin cup and vacuumed baked to remove residual solvent.

Alternatively, the erodible mask can be made of a material having a variable composition such that predefined regions of the mask selectively absorb greater amounts of laser radiation even though the entire mask has a uniform thickness. Again, materials such as PMMA and PS can be employed in varying concentrations in the erodible mask to achieve the variable composition of the mask.

Figure 3:
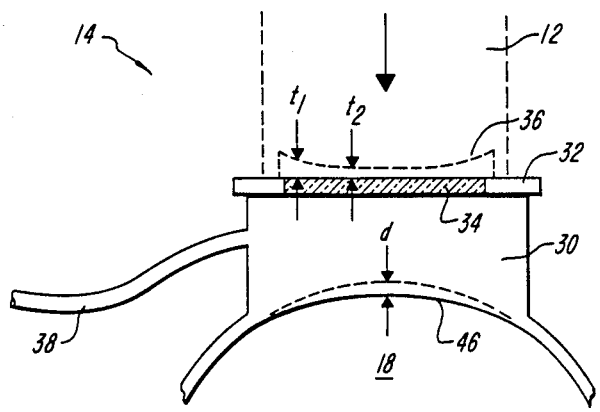
FIG. 3 illustrates diagramatically the method of the present invention in reducing the curvature of an object.

FIG. 3 illustrates the principle involved in eroding a surface to effect reprofiling thereof in accordance with the present invention. Although the transparent stage shown in the figures is substantially horizontal, it should be clear that it can also take other shapes (e.g., concave or convex spherical forms) and can further include a cup-shaped rim to support a liquid or semi-liquid masking lens.

In FIG. 3, the reference 18 denotes the object such as the cornea of an eye to be reprofiled and, reference 36 denotes a masking lens disposed over the area thereof to be treated. Also as indicated in FIG. 3, the lens 36 is uniformly irradiated with a beam of radiation 12 obtained from a pulsed UV laser source.

During the irradiation, the lens 36 is gradually ablated, and an increasing area of the object 18 becomes exposed to erosion. As indicated in FIG. 3 at the moment when the lens has been wholly ablated, the surface of the object has been eroded as indicate at 46, to the extent necessary to complete reprofiling over the area of the lens. As shown in FIG. 3, the maximum thickness $t_1$ of the lens 36 exceeds the minimum thickness $t_2$ by an amount equal to the maximum depth (d) of the object erosion desired.

The present invention is especially suited to the treatment of cornea of an eye and provides a less dramatic means of effecting reprofiling of the cornea, for example, as a remedy for certain forms of refractive errors. FIGS. 2 and 3 illustrate the methods of the present invention in connection with the treatment of myopia (nearsightedness). Similar lenses of appropriate shape can, of course, be employed to remedy other forms of reflective errors, such as hyperopia and astigmatism.

Figure 4:
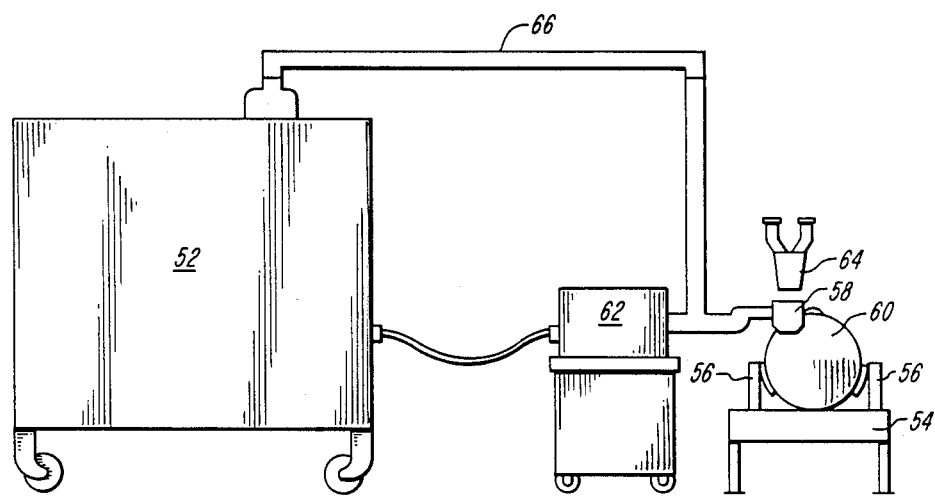
FIG. 4 shows a laser apparatus for measurement and reprofiling.

FIG. 4 illustrates an apparatus for performing a method of the present invention for reprofiling the cornea of a human eye. A laser and associated control circuitry is contained in a housing 52. The beam-forming optics, for providing a beam of desired shape and size, can also be contained within the housing 52 together with the laser power supply control circuits. An optical wave guide 66, which can be flexible or rigid and includes suitable mirrors, prisms and lenses, is provided to transmit the laser beam output from the housing 52 to the patient 60. The patient 60 is lying face-upwards on an operating table 54. The operating table 54 will support the patient's head against vertical movement. If desired, side supports 56 may also be provided to restrain sideways movement of the patient's head.

The erodible mask of the present invention is disposed within an eyepiece 50A adapted to fit over the patient's eye. The eyepiece 58 includes suction means for providing suction to clamp the eyepiece over the patient's eye. The eyepiece can include a cup of resiliently deformed flexible material such as rubber or plastic, which when placed over the eyeball will clamp thereto upon being evacuated. Also disposed within the eyepiece are suitable optical elements for transmitting the laser radiation to the surface of the eye, and the erodible mask similar in structure to the erodible mask shown in FIG. 2 and FIG. 3 above. The erodible mask is manufactured as described above based on measurements of the patient's eye and has an profile which will impart the desired refraction correction upon erosion.

During the operation, the eye can be observed using a surgical microscope 64 which is supported above the patient by any convenient means. The surgical microscope 64 may be connected to the eyepiece 58, but will more normally be separated therefrom and supported by an arm (not shown) from the ceiling or by a cantilever (not shown).

A measuring device 62 can also be employed in conjunction with the present apparatus to measure the changes in the curvature of the cornea following operation. Such a measuring device 62 can also be employed to monitor the degree of erosion of the mask during treatment. The measuring device can take the form of a commercially-available keratometer or other suitable device and can be connected, as shown in FIG. 5, directly to the laser optical path or may be movable when needed to occupy the position shown for the surgical microscope 64, the operator moving the measuring device 62 or the microscope 64 into position as required.

The measuring device 62 can further provide the feedback control, as shown in FIG. 1, whereby information from optical or other inspection of the surface which is being exposed to laser erosion is used to control the actual duration and amplitude of the pulses supplied by the laser and may be tuned so as to produce just the desire degree of erosion of the surface by each pulse.

I claim:

1. A masking apparatus for use in laser reprofiling of corneal tissue comprising a rigid support structure having a surface shaped for fixation upon an eye having a cornea, and a mask connected to an opposite surface of the support structure and adapted to be disposed above the cornea, the mask having a predefined profile of resistance to erosion by laser radiation, whereby upon irradiation of the mask, a portion of the laser is selectively absorbed and another portion is transmitted to the cornea in accordance with the mask profile to selectively erode the tissue.

2. The apparatus of claim 1 wherein the support structure further includes a transparent stage means for receiving the mask.

3. The apparatus of claim 1 wherein the mask is a lens which varies in thickness to provide the profile.

4. The apparatus of claim 1 wherein the mask is a lens which varies in composition to provide the profile.

5. The apparatus of claim 1 wherein the mask is formed from poly(methyl methacrylate), poly(methyl styrene), or mixtures thereof.

* * * * *